(12) United States Patent
Sater

(10) Patent No.: US 7,438,716 B2
(45) Date of Patent: Oct. 21, 2008

(54) CONTROL APPARATUS FOR ACTUATING AN ELONGATE MEDICAL SHAFT

(75) Inventor: Ghaleb A. Sater, Lynnfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 722 days.

(21) Appl. No.: 10/698,796

(22) Filed: Oct. 30, 2003

(65) Prior Publication Data

US 2005/0096663 A1    May 5, 2005

(51) Int. Cl.
*A61F 11/00* (2006.01)
*A61M 29/00* (2006.01)

(52) U.S. Cl. .................................. 606/108; 606/200
(58) Field of Classification Search .................. 74/130, 74/77, 128, 141.5
See application file for complete search history.

(56) References Cited

U.S. PATENT DOCUMENTS 96,880 A * 11/1869 Bull ........................... 74/141.5

FOREIGN PATENT DOCUMENTS

DE    1258391 A2 * 4/2002

\* cited by examiner

*Primary Examiner*—Corrine McDermott
*Assistant Examiner*—Christopher D Prone
(74) *Attorney, Agent, or Firm*—James F Crittenden

(57) ABSTRACT

Methods and apparatus are provided for moving an intraluminal filament, such as a shaft or hypotube. The actuator includes a housing having a channel therein, the channel having at least a first inclined surface. The actuator also includes a pivotable actuator assembly coupled to the housing and having first and second spaced-apart jaws extending into the channel. The first and second jaws define an opening of a first dimension therebetween. The actuator assembly pivots for urging at least one of the first and second jaws against at least the first inclined surface to transition the first dimension to a second dimension. The method comprises aligning the intraluminal filament between spaced-apart jaws of a pivotable actuator assembly, pivoting the actuator assembly to urge said jaws against at least one surface causing said jaws to grip the intraluminal filament, and further pivoting the actuator assembly to move the intraluminal filament.

12 Claims, 4 Drawing Sheets

CONTROL APPARATUS FOR ACTUATING AN ELONGATE MEDICAL SHAFT

FIELD OF THE INVENTION

The present invention relates generally to intraluminal devices, and more particularly, to a control assembly for moving a shaft of an intraluminal medical device.

BACKGROUND OF THE INVENTION

Stenotic lesions may comprise a hard, calcified substance and/or a softer thrombus material, each of which forms on the lumen walls of a blood vessel and restricts blood flow therethrough. Intraluminal treatments such as balloon angioplasty, stent deployment, atherectomy, and thrombectomy are well known and have proven effective in the treatment of such stenotic lesions. These treatments often involve the insertion of a therapy catheter into a patient's vasculature.

Distal protection devices (DPDs) such as filters and occluders represent one class of vasculature catheters used in the treatment of stenotic lesions. Filter devices are positioned distally from a stenotic lesion to capture stenotic debris that may be released during intraluminal treatments such as balloon angioplasty or thrombectomy. An occluder device is positioned distally from a stenotic lesion and may be used to block stenotic debris released during an intraluminal treatment, to catch a blood clot when pulled from a blood vessel, and the like.

One type of DPD utilizes a "push/pull" mechanism to deploy the apparatus at the distal end of the DPD. This type of DPD comprises an inner member such as a core wire or guide wire housed within an outer hollow sheath or hypo tube. Either the core wire or the hypo tube is attached to, for example, a filter of the filter device or an occluder device. During an intraluminal treatment, the DPD is inserted into a patient's blood vessel until the filter or occluder is located distally of the lesion. By coaxially pushing or pulling the core wire and/or hypo tube relative to each other, the filter or occluder is expanded to an operational diameter. Once treatment is completed, the core wire and/or hypo tube is again coaxially pulled or pushed relative to each other and the filter or occluder is contracted to a removable diameter, and the DPD is removed from the patient.

Deployment of DPDs that utilize push/pull mechanisms may be damaging to the DPD. Certain DPD devices utilize fine core wire, such as those having a diameter of 0.013 inches or less, and fine hypo tubes, such as those having a diameter of 0.014 inches or less, both of which may be easily crimped or kinked. In addition, such DPDs may require significant force (e.g. one or more pounds) to move the hypo tube relative to the core wire, especially when the DPD is disposed in torturous vasculature. Further, surgical-grade coatings may be applied to such devices for a variety of purposes, such as to reduce trauma to surrounding tissue and/or to reduce risk of infection. If precautions are not taken, the coating may be scraped off the devices during deployment.

Other intraluminal devices also utilize coaxial push and/or pull mechanisms for deployment. For example, one class of self-expanding tubular stents is mounted on an inner catheter and is held in a collapsed configuration by a slidable shaft or sheath. Typically, the stent is released in a blood vessel by sliding the sheath off the stent while holding the inner catheter in a fixed longitudinal position in the patient. Current methods for deploying the stent, however, such as sliding thumb buttons and telescoping hypodermic tubes may cause unintentional advancement of the inner catheter through the sheath and, hence unintentional misplacement of the stent.

Thus, it should be clear, that a need exists for the precise controllability of the movement of medical shafts (e.g. guide wires, hypo tubes, etc.) during intraluminal procedures of the type described above in order to achieve precise placement and deployment of the intraluminal device. Furthermore, since an operator may be required to perform or monitor several tasks simultaneously, it would be desirable that the precise movement and positioning of the intraluminal be performed with one hand.

Accordingly, it would be desirable to provide an intraluminal device actuator configured for one-handed operation which results in precise movement and deployment of the intraluminal device. Other desirable features in characteristics of the present invention will become apparent from the subsequent detailed description and the appended claims taken in conjunction with the accompanying drawings.

BRIEF SUMMARY OF THE INVENTION

According to an aspect of the present invention there is provided an actuator for moving an intraluminal shaft. The actuator includes a housing having a channel through at least a portion thereof, the channel having at least a first inclined surface therein. A pivotal actuator assembly is coupled to the housing and has first and second spaced-apart jaws extending into the channel. The first and second jaws define an opening of a first dimension therebetween, and the actuator assembly urges at least one of the first and second jaws against the inclined surface to alter the dimension of the opening between the first and second jaws.

According to a further aspect of the invention there is provided a method for moving an intraluminal shaft. The intraluminal shaft is aligned between spaced-apart jaws of a pivotable actuator assembly which extends into a channel of a housing. The actuator assembly is then pivoted to urge the space-apart jaws against at least one deflecting surface in the channel causing the spaced apart jaws to grip the intraluminal shaft. Further pivoting of the actuator assembly moves the intraluminal shaft.

BRIEF DESCRIPTION OF THE DRAWINGS

The following drawings are illustrative of the particular embodiments of the invention and therefore do not limit its scope. They are presented to assist in providing a proper understanding of the invention. The drawings are not to scale and are intended for use in conjunction with the explanations in the following detailed descriptions. The present invention will hereinafter be described in conjunction with the appending drawings, wherein like reference numerals denote like elements, and.

DETAILED DESCRIPTION OF THE INVENTION

Figure 1:
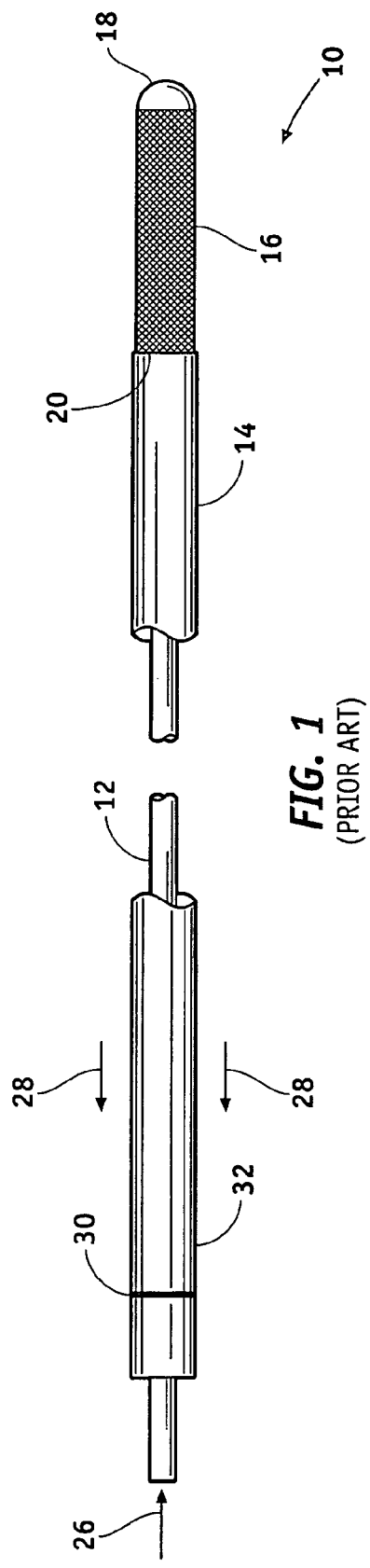
FIG. 1 is side view of a distal protection device including a filter in a collapsed configuration.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The various embodiments of the present invention include an actuator for moving an intraluminal shaft of any suitable intraluminal device that utilizes a push and/or pull procedure for the deployment or collapsing of an expandable apparatus such as an expandable filter, occluder, stent, balloon, etc., which is located at a first (distal) end of the intraluminal device. In one class of such intraluminal devices such as filters, occluders, and funnel shaped devices, an outer member of the device such as a sheath or hollow tube is pushed away from the clinician to expand the apparatus for deployment in an operational mode. In certain of these devices when the sheath or tube is pulled toward the clinician, the apparatus is collapsed such as when the device is removed from a patient's vasculature. In another class of such intraluminal devices such as self-expanding stents, when the sheath or tube is pulled towards the clinician, the apparatus is allowed to expand for deployment in an operational mode.

One example of intraluminal devices that operate in conjunction with such push and/or pull mechanisms suitable for use in conjunction with the present invention includes distal protection devices (DPDs). One exemplary DPD is an expandable filter device 10 shown in FIGS. 1 and 2. It should be appreciated however that other types of DPDs (e.g. occluders) may also be utilized. Expandable filter device 10 includes an inner member, such as a core wire or guide wire, and an outer hollow member 14, such as a sheath or a hypo tube, moveably disposed thereabout. Core wire 12 extends beyond hypo tube 14 at the proximal end 32 of hypo tube 14. A filter apparatus 16 surrounds core wire 12 and has a distal end fixed to a core wire distal end 18 and a proximal end fixed to a hypo tube distal end 20. To expand filter apparatus 16, core wire 12 is pulled and/or hypo tube is pushed, as shown by arrows 22 and 24 respectively in FIG. 2. The relative displacement of core wire 12 and hypo tube 14 moves the ends of filter apparatus 16 towards each other thus forcing the middle region of filter apparatus 16 to expand. To collapse filter apparatus 16, core wire 12 is pushed and/or hypo tube 14 is pulled as shown by the arrows 26 and 28 respectively in FIG. 1. This reverse manipulation draws the ends of filter apparatus apart pulling the middle region of filter apparatus radially inward towards core wire 12.

Figure 2:
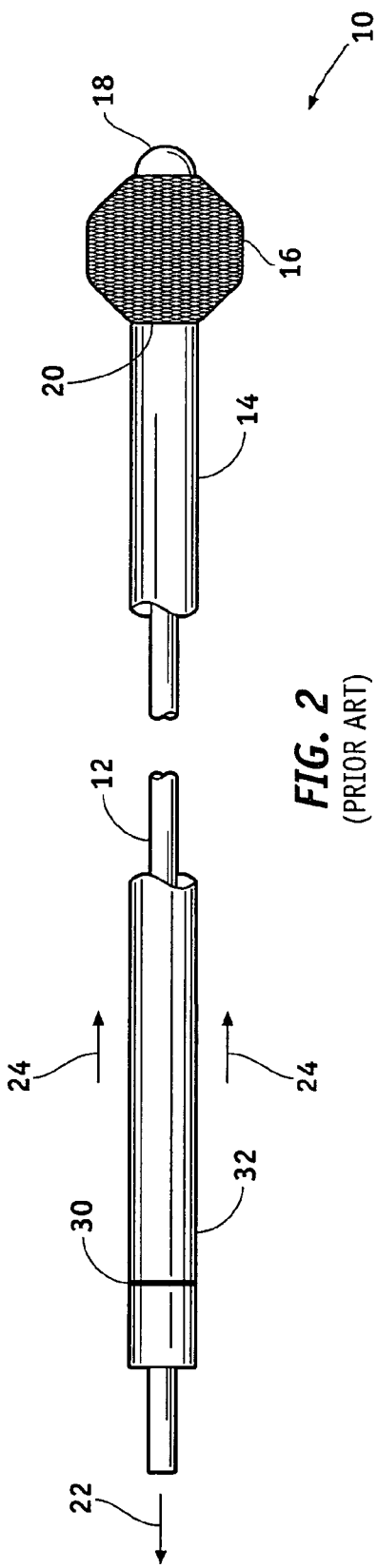
FIG. 2 is a side view of the distal protection device shown in FIG. 1 with the filter in a deployed configuration.
Figure 3:
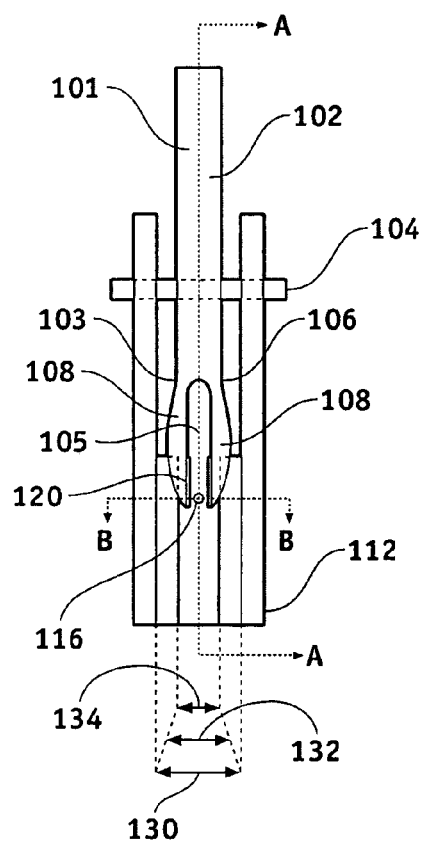
FIG. 3 is an end view of an exemplary intraluminal actuator in accordance with a first embodiment of the present invention.
Figure 4:
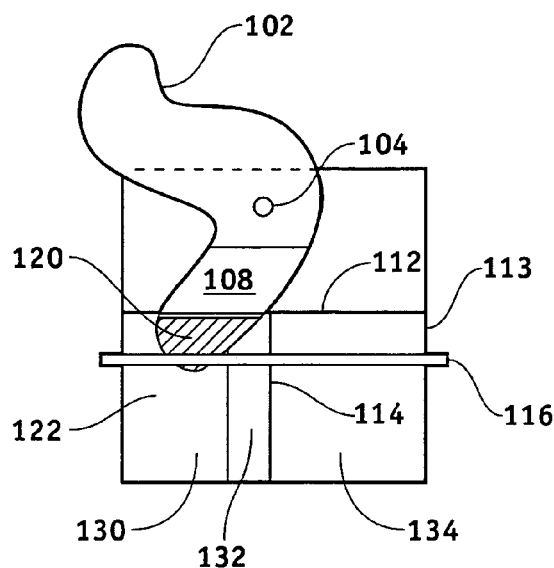
FIG. 4 is a side cross-sectional view of the exemplary intraluminal device actuator shown in FIG. 3 taken along line A-A.

Dimensions of these types of intraluminal devices may be quite small. For example, for some devices, the diameter of the core wire may be as small as 0.013 inches or smaller. Similarly, diameter of the hypo tube may be 0.014 inches or smaller. Due to such small dimensions, it is often difficult for a clinician to see the proximal end of the hypo tube. Thus, as illustrated in FIGS. 1 and 2, such intraluminal devices may comprise a marker 30 that is positioned at proximal end 32 of the hypo tube; i.e. the end opposite the filter apparatus end. Thus, it should be appreciated that it would be desirable to provide an intraluminal device actuator which enables the precise manipulation of an intraluminal shaft such as a guide wire or hypo tube.

FIGS. 3-6 illustrate a first embodiment of the inventive intraluminal actuator. Referring to FIGS. 3-6, the exemplary intraluminal actuator includes a housing 112 and an actuator assembly or lever 102 pivotably mounted therein as is shown by pivot 104. Housing 112 has a channel 122 which extends through at least a portion of housing 112 and comprises three regions substantially aligned along a longitudinal axis. These regions include a release region 130, a transition region 132, and an engagement region 134. Actuator assembly 102 includes a handle portion 101 accessable from the exterior of housing 112 and a gripping portion 103 which extends into housing 112 and channel 122. Gripping portion 103 includes opposed, spaced-apart jaws or prongs 108 which include outer surfaces 106. Spaced-apart jaws 108 may also include gripping adaptations 120 on their inner surfaces. For example, the inner surfaces may be roughened or provided with a resilient material attached thereto. As stated previously, spaced-apart jaws 108 of actuator assembly 102 extend into channel 122.

Release region 130 of channel 122 has a width greater than the outside width of spaced-apart jaws 108 such that the interior surfaces of channel 122 do not contact or deflect jaws 108 in a release region 130. Furthermore, spaced-apart jaws 108 define an opening 105 therethrough having a width which is greater than the outer diameter of an intraluminal shaft 116 (e.g. guide wire, hypo tube, or the like) which passes longitudinally through opening 105 between spaced-apart jaws 108.

Transition region 132 includes inclined surfaces 114 which extend from release region 130 to engagement region 134. As can be seen, inclined surfaces 114 of transition region 132 narrow the width of channel 122 so as to create an engagement region 134 having a width smaller than that of release region 130. Thus, as actuator 102 is pivoted by moving handle 101 in a counter-clockwise direction as viewed in FIG. 4, spaced-apart jaws 108 engage inclined surfaces 114 and deflect, causing opening 105 to decrease in size. This closing motion of jaws 108 results in a gripping of filament or shaft 116. Further movement of gripping portion 103 towards and into gripping section 134 results in longitudinal movement of shaft 116 with respect to housing 112. Moving handle 101 back in a clockwise direction will return shaft 116 in an opposite direction until jaws 108 release shaft 116. It should be clear that inclined surfaces 114 may be flat or curved. It is only necessary that surfaces 114 impart a smooth closing motion of jaws 108 onto filament or shaft 116. Furthermore, while the embodiment shown in FIGS. 3-6 illustrate two inclined surfaces 114, it should be clear that only one inclined surface may be necessary to deflect one of jaws 108 to reduce the dimension of opening 105. Furthermore, while FIGS. 3-6 illustrate the interior surfaces of channel 122 as being flat, one or more of regions 130, 132, and 134 may be bound by curved, faceted, or hybrid interior surfaces.

Figure 5:
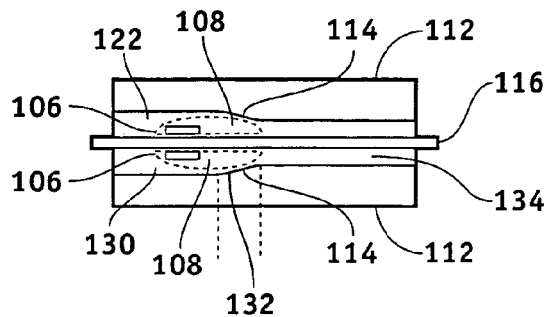
FIG. 5 is a top cross-sectional view of the exemplary intraluminal device actuator shown in FIG. 3 taken along line B-B showing the actuator in a non-gripping configuration.
Figure 6:
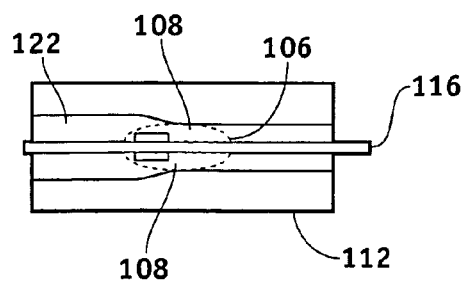
FIG. 6 is a top cross-sectional view of the exemplary intraluminal device actuator shown in FIG. 3 showing the actuator in a gripping configuration.
Figure 8:
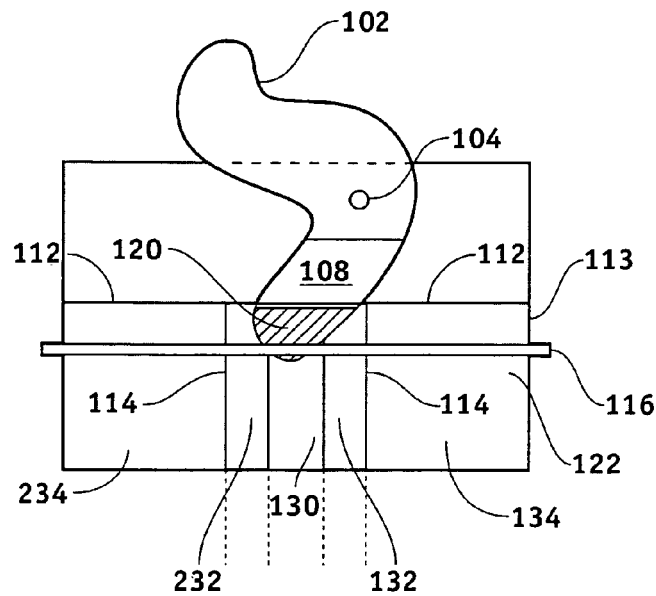
FIG. 8 is a side cross-sectional view of the exemplary intraluminal device actuator shown in FIG. 7 taken along line C-C.
Figure 7:
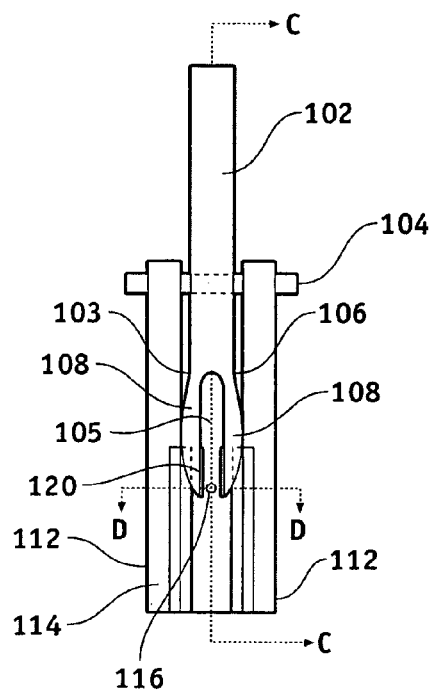
FIG. 7 is a end view of an exemplary intraluminal device actuator in accordance with a second embodiment of the present invention.
Figure 9:
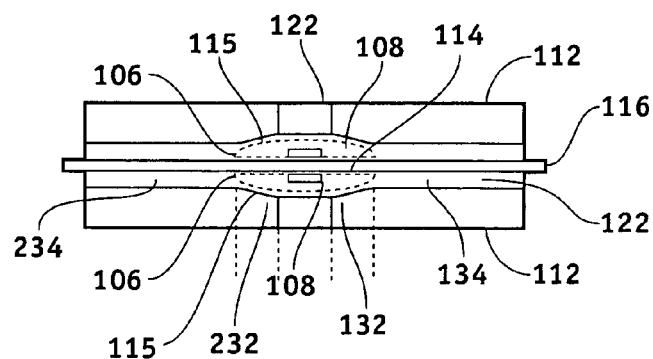
FIG. 9 is a top cross-sectional view of the exemplary intraluminal device actuator shown in FIG. 7 taken along line D-D showing the actuator in a non-gripping configuration.

Actuator assembly 102 pivots on pivot 104 to move opposed spaced-apart jaws 108 of actuator assembly 102 through regions 130, 132, and 134. The shaft 116 to be moved is aligned in channel 122 substantially between spaced-apart jaws 108 and generally along a longitudinal axis of channel 122. In release region 130, opposed jaws 108 do not cause movement of shaft 116. As actuator assembly 102 pivots about pivot 104 in a counter clockwise direction (FIG. 4), the outer surfaces 106 of spaced-apart jaws 108 engage inclined surfaces 114 in transition region 132 as is shown in FIG. 5. The engagement of outer surfaces 106 of spaced-apart jaws 108 with inclined surfaces 114 of transition region 132 urges jaws 108 towards each other thereby gripping shaft 116 as is shown in FIG. 6. Further pivoting translates jaws 108 along channel 122 thereby moving gripped shaft 116 with respect to housing 112. The movement of actuator assembly 102 may be limited by a surface of housing 112 (e.g. end surface 113) shown in FIG. 4, or by other suitable obstructions to prevent further pivoting.

Some vertical movement of flexible shaft 116 may be intrinsic to the pivoting actuator 102. Such vertical movement may be minimized in several ways. For example, an alignment bore (e.g. of a type shown in FIG. 11 and designated 121) may be associated with opening 117 in housing 112 to remove vertical components of motion from shaft 116 at the exterior of the intraluminal actuator. Alternatively, a four-bar mechanism may be used as an actuator to reduce vertical motion of shaft 116 during translation. Yet another alternative for minimizing vertical motion of shaft 116 may involve the use of a cam in the pivoting mechanism.

While two opposed jaws 108 are utilized in the actuator shown in FIGS. 3-6, it should be appreciated that alternative gripping configurations may be utilized. For example, a single jaw 108 may be used to grip shaft 116 between a jaw 108 and an interior surface of channel 122. In yet another arrangement, a single movable jaw 108 may be utilized in conjunction with an opposed immoveable jaw. Furthermore, if desired, more than two jaws may be used.

Figure 10:
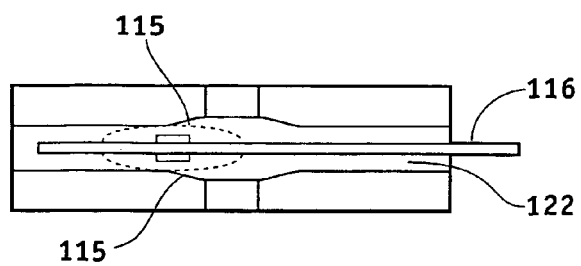
FIG. 10 is a top cross-sectional view of the exemplary intraluminal device actuator shown in FIG. 7 showing the actuator in a gripping configuration.

FIGS. 7-10 illustrate an exemplary bidirectional intraluminal device actuator in accordance with the present invention having a second transition region 232 and a second engagement region 234 aligned with the longitudinal axis of channel 122 and extending from release region 130 in a direction generally opposite to transition region 132 and engagement region 134. In this embodiment, the shaft 116 can be extended or retracted relative to a starting position utilizing the principles described above. That is, in the previous embodiment, pivoting actuator assembly 102 about pivot 104 in a counter-clockwise direction caused gripping portion 103 to move from release section 130 into transition section 132 to engage shaft 116 and impart longitudinal movement to shaft 116 to the right (as shown in FIG. 6). By pivoting actuator 102 in a clockwise direction, gripping portion 103 will enter second transition region 232 which causes outer surfaces 106 of space-apart jaws 108 to engage inclined surfaces 115 thereby gripping shaft 116. Further movement of actuator 102 in a clockwise direction will cause shaft 116 to move to the left (as shown in FIG. 10). Thus, shaft 116 may be extended or retracted relative to a starting position; for example, relative to the entrance of a hypo tube.

Figure 11:
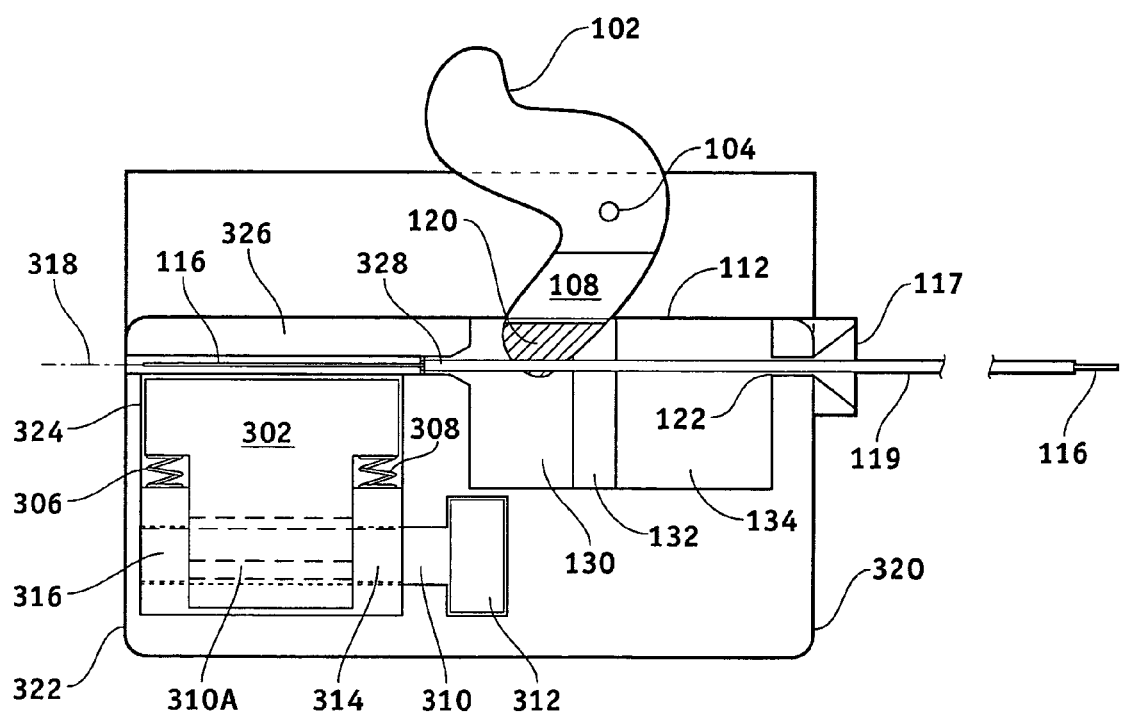
FIG. 11 is a side cross-sectional view of the exemplary intraluminal device actuator in accordance with a still further embodiment of the present invention.

FIG. 11 is a cross sectional view of a control handle apparatus for an intraluminal device which permits relative movement between a hollow shaft or hypo tube 119 and a guide wire 116 mounted for translational movement within hypo tube 119. The control handle comprises housing 112 having a longitudinal axis 318, a first end 320, and a second end 322. At first end 320 of housing 112, the control handle includes an entry port 117 configured to receive an inner member, such as core wire 116, and an outer member such as hypo tube 119 of an intraluminal device. Entry port 117 is coupled to channel 122 which is parallel to longitudinal axis 318 and which extends from entry port 117 to the second end 322 of housing 112. It should be appreciated, however, that channel 122 may terminate at any point beyond a clamp assembly 302 which will be discussed in more detail below. Housing 112 may be formed of any suitable engineering-grade polymers or metals. Examples of suitable polymers include polycarbonates, nylon, styrene copolymers, and the like. Suitable metals may include stainless steel, aluminum, and the like.

As can be seen, the proximal side of housing 112 is similar to the actuator described above in connection with FIGS. 3-6, and like elements have been denoted with like reference numerals. Thus, actuator 102 is capable of moving hypo tube 119 in first and second directions relative to core wire 116 as described earlier when core wire 116 is clamped as described above.

The control handle further comprises a clamp assembly 302 positioned proximate to the second end 322 of housing 112. Clamp assembly 302 comprises a first clamp element 324 and a second clamp element 326 which are aligned to mate about an axis parallel to longitudinal axis 318. First clamp element 324 may comprise a press block, and second clamp element 326 may comprise a portion of housing 112, although it should be appreciated that second clamp element 326 may comprise a unit or device separate from housing 112. Clamp assembly 302 may further comprise at least a first clamp pillow block 314 and a second clamp pillow block 316. First clamp element 324 is biased by clamp block springs 308 and 306 respectively. The first and second clamp block springs 306 and 308 are preferably compression springs. Thus, first clamp element 324 is configured to move relative to first and second clamp pillow blocks 314 and 316 which remain stationary relative to housing 112.

The control handle also comprises a closure mechanism 312 which may comprise a cam shaft 310 and a cam lever 312. Cam shaft 310 extends parallel to longitudinal axis 318 and is connected to cam lever 312. Cam shaft 310 extends through first clamp pillow block 314, first clamp element 324, and second clamp pillow block 316. The section of cam shaft 310 that extends through first clamp element 324 comprises a cam lobe 310*a* formed by an offset portion. That is, lobe 310*a* may be formed as a flat or convex undercut portion in an otherwise cylindrical cam shaft 310.

Core wire 116 is coaxially movably disposed within hypo tube 119 and extends beyond hypo tube 119 at a proximal end 328 of the intraluminal device which as been positioned within housing 112. Rotation of cam shaft 310 causes lobe 310*a* to act against a through bore in first clamp 324 such that the first clamp slides between first clamp pillow block 316 and second clamp pillow block 314 and compresses first and second clamp block springs 306 and 308. Thus, rotation of clamp lever 312 in one direction causes first clamp member 324 to move a sufficient distance from second clamp member 326 so as to allow core wire 116 to be interposed between the first and second clamp elements 324 and 326.

The transverse dimension of channel 122 from first end 320 of housing 112 to second end 322 is sufficiently wide to receive core wire 116 and hypo tube 119 although it will be appreciated that the transverse dimension of the channel may vary from first end 320 to second end 322. End 328 of the intraluminal device may now be inserted into entry port 117. That is, core wire 116 may first be inserted into entry port 117 followed by hypo tube 119.

After the intraluminal device has been suitably positioned within housing 112 with core wire 116 interposed between first clamp element 324 and second clamp element 326 and hypo tube 119 interposed between spaced-apart jaws 108, the clamp may be closed. This is accomplished by releasing cam lever 312 from its open position. When cam lever 312 is closed, cam shaft 310 also causes cam lobe 310a to be rotated out of engagement with the through bore in first clamp element 324 thus permitting first and second clamp block springs 306 and 308 to expand such that first clamp element 324 slides between first clamp pillow block 314 and second clamp pillow block 316. Thus, first clamp element 324 is caused to advance towards second clamp element 326 to decrease the transverse dimension of the channel between the first and second clamp elements 324 and 326 thus securing guide wire 116 between the first and second clamp elements 324 and 326 respectively. Once the intraluminal device has been secured within housing 112. Hypo tube 119 may be moved relative to core wire 116 by manipulation of actuator 102 as previously described.

Thus, there has been provided a simple intraluminal actuator which may be operated using only one hand and functions to move a shaft of an intraluminal device.

While at least one exemplary embodiment has been presented in the foregoing detailed description, it should be appreciated that a vast number of variations exist. For example, the embodiment shown in FIG. 11 may be configured such that the first and second clamp elements 324 and 326 clamp hypo tube 119, and jaws 108 engage core wire 116, so as to move core wire 116 relative to hypo tube 119. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A control apparatus for moving an intraluminal shaft of a medical device, the apparatus comprising:
   a housing having a longitudinally extending channel through at least a portion thereof, said channel having at least a first surface substantially inclined along a longitudinal direction; and
   an actuator movably mounted to the housing, the actuator being coupled to first and second spaced-apart jaws disposed in the channel, the jaws being adapted for releasably gripping a shaft extending longitudinally through the channel, said first and second jaws defining an opening of a first dimension therebetween for receiving the shaft, said actuator being movable to urge at least one of said first and second jaws longitudinally along said first substantially inclined surface to transition said first dimension to a second dimension adapted to grip the shaft, whereby continued movement of the actuator may cause longitudinal movement of the shaft.

2. The apparatus according to claim 1, wherein said second dimension is smaller than said first dimension.

3. The apparatus according to claim 2, wherein the second dimension of said opening corresponds to a gripping dimension between said first and second spaced-apart jaws, and said first dimension corresponds to a release dimension between said first and second spaced-apart jaws.

4. The apparatus according to claim 3, wherein said channel comprises:
   a release region;
   a first gripping region; and
   a first transition region between said release region and said gripping region, said first transition region including said first substantially inclined surface.

5. The apparatus according to claim 4, wherein said release region has a width greater than an outside width of said first and second spaced-apart jaws.

6. The apparatus according to claim 5, wherein said first gripping region has a width substantially equal to said outside width of said first and second spaced-apan jaws.

7. The apparatus according to claim 4, wherein said first substantially inclined surface comprises a curved surface.

8. The apparatus according to claim 4, wherein said first transition region further comprises at least a second substantially inclined surface, said first and second inclined surfaces for engaging said spaced-apart jaws respectively to reduce said first dimension.

9. The apparatus according to claim 1, wherein said channel has at least one surface positioned to limit motion of said actuator assembly.

10. A control apparatus for moving a shaft of an intraluminal medical device in a first, longitudinal direction, the apparatus comprising:
    a housing having a longitudinally extending channel through at least a portion thereof and having at least a first surface substantially inclined along a longitudinal direction said channel being dimensioned to receive said medical shaft therein; and
    an actuator movably mounted to said housing, the actuator being coupled to first and second spaced-apart jaws extending into said channel, the jaws defining an opening therebetween for receiving and releasably gripping said medical shaft, said channel further comprising:
    a release region wherein said spaced-apart jaws do not engage said medical shaft;
    a first engagement region wherein said spaced-apart jaws grip said medical shaft; and
    a first transition region between said release region and said first engagement region for urging said spaced-apart jaws into engagement with said medical shaft.

11. An apparatus according to claim 10, wherein said first transition region comprises first and second substantially opposed inclined surfaces separated by a first dimension proximate said release region and separated by a second dimension proximate said first engagement region, said second dimension being smaller than said first dimension.

12. An apparatus according to claim 11, wherein movement of said first and second spaced apart jaws in a first direction causes said first and second spaced-apart jaws to move from said release region, through said first transition region to grip said medical shaft, and into said first engagement region to translationally move said medical shaft in said first direction.

* * * * *